(12) United States Patent
von Oepen et al.

(10) Patent No.: US 11,679,236 B2
(45) Date of Patent: Jun. 20, 2023

(54) MECHANICAL INTERLOCK FOR CATHETERS

(71) Applicant: Cephea Valve Technologies, Inc., Santa Clara, CA (US)

(72) Inventors: Randolf von Oepen, Aptos, CA (US); Sean A. McNiven, Menlo Park, CA (US); Francisco Valencia, East Palo Alto, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 388 days.

(21) Appl. No.: 16/842,229

(22) Filed: Apr. 7, 2020

(65) Prior Publication Data
US 2020/0230354 A1 Jul. 23, 2020

Related U.S. Application Data

(62) Division of application No. 15/662,076, filed on Jul. 27, 2017, now Pat. No. 10,646,689.
(Continued)

(51) Int. Cl.
*A61M 25/01* (2006.01)
*A61M 25/00* (2006.01)
(Continued)

(52) U.S. Cl.
CPC .... *A61M 25/0051* (2013.01); *A61B 17/00234* (2013.01); *A61F 2/2427* (2013.01);
(Continued)

(58) Field of Classification Search
CPC .... A61M 25/00; A61M 25/01; A61M 25/005; A61M 25/0662; A61M 25/0141; A61M 25/0051; A61B 17/00; A61B 17/00234
See application file for complete search history.

(56) References Cited

U.S. PATENT DOCUMENTS

| | | |
|---|---|---|
| 4,406,656 A | 9/1983 | Hattler et al. |
| 4,728,319 A | 3/1988 | Masch |

(Continued)

FOREIGN PATENT DOCUMENTS

| | | |
|---|---|---|
| CN | 1469724 | 1/2004 |
| CN | 1688352 A | 10/2005 |

(Continued)

OTHER PUBLICATIONS

Hironobu Takizawa et al. "Development of a Microfine Active Bending Catheter Equipped with MIF Tactile Sensors", Micro Electro Mechanical Systems, IEEE, Jan. 17, 1999, pp. 412-417.
(Continued)

*Primary Examiner* — Vi X Nguyen
(74) *Attorney, Agent, or Firm* — Workman Nydegger

(57) ABSTRACT

An intravascular device delivery system has an elongated member with a flexible hypotube. The hypotube can be rotationally keyed to a steerable catheter. The flexible hypotube includes one or more cuts to allow bending of the flexible hypotube within a first plane. The steerable catheter is steerable to bend the flexible hypotube within the first plane, and longitudinally movable relative to the flexible hypotube to allow distal movement of the steerable catheter relative to a distal end of the flexible hypotube.

12 Claims, 11 Drawing Sheets

Related U.S. Application Data

(60) Provisional application No. 62/462,776, filed on Feb. 23, 2017, provisional application No. 62/436,887, filed on Dec. 20, 2016, provisional application No. 62/380,246, filed on Aug. 26, 2016, provisional application No. 62/368,711, filed on Jul. 29, 2016.

(51) Int. Cl.
*A61B 17/00* (2006.01)
*A61F 2/24* (2006.01)
*A61M 25/06* (2006.01)

(52) U.S. Cl.
CPC .... *A61M 25/0102* (2013.01); *A61M 25/0136* (2013.01); *A61M 25/0138* (2013.01); *A61M 25/0141* (2013.01); *A61M 25/0147* (2013.01); *A61B 2017/00243* (2013.01); *A61B 2017/00309* (2013.01); *A61B 2017/00323* (2013.01); *A61B 2017/00477* (2013.01); *A61B 2017/00526* (2013.01); *A61B 2017/00783* (2013.01); *A61B 2017/00991* (2013.01); *A61M 25/005* (2013.01); *A61M 25/0045* (2013.01); *A61M 25/0662* (2013.01); *A61M 2025/0004* (2013.01); *A61M 2025/0006* (2013.01); *A61M 2025/0063* (2013.01); *A61M 2025/0161* (2013.01); *A61M 2025/0175* (2013.01); *A61M 2025/0681* (2013.01)

(56) References Cited

U.S. PATENT DOCUMENTS

| | | |
|---|---|---|
| 5,053,043 A | 10/1991 | Gottesman et al. |
| 5,059,213 A | 10/1991 | Chesterfield et al. |
| 5,078,722 A | 1/1992 | Stevens |
| 5,078,723 A | 1/1992 | Dance et al. |
| 5,236,450 A | 8/1993 | Scott |
| 5,325,845 A | 7/1994 | Adair |
| 5,345,945 A | 9/1994 | Hodgson et al. |
| 5,387,219 A | 2/1995 | Rappe |
| 5,415,664 A | 5/1995 | Pinchuk |
| 5,472,423 A | 12/1995 | Gronauer |
| 5,571,085 A | 11/1996 | Accisano, III |
| 5,662,606 A | 9/1997 | Cimino et al. |
| 5,669,919 A | 9/1997 | Sanders et al. |
| 5,769,812 A | 6/1998 | Stevens et al. |
| 5,807,405 A | 9/1998 | Vanney et al. |
| 5,820,591 A | 10/1998 | Thompson et al. |
| 5,843,103 A | 12/1998 | Wulfman |
| 5,855,601 A | 1/1999 | Bessler et al. |
| 5,873,882 A | 2/1999 | Straub et al. |
| 5,902,334 A | 5/1999 | Dwyer et al. |
| 5,906,642 A | 5/1999 | Caudillo et al. |
| 5,957,973 A | 9/1999 | Quiachon et al. |
| 6,090,118 A | 7/2000 | McGuckin, Jr. |
| 6,180,059 B1 | 1/2001 | Divino, Jr. et al. |
| 6,228,110 B1 | 5/2001 | Munsinger |
| 6,458,137 B1 | 10/2002 | Klint |
| 6,517,550 B1 | 2/2003 | Konya et al. |
| 6,695,836 B1 | 2/2004 | DeMello et al. |
| 6,926,725 B2 | 8/2005 | Cooke et al. |
| 7,172,617 B2 | 2/2007 | Colgan et al. |
| 7,344,553 B2 | 3/2008 | Opolski et al. |
| 7,666,204 B2 | 2/2010 | Thornton et al. |
| 7,736,388 B2 | 6/2010 | Goldfarb et al. |
| 7,837,727 B2 | 11/2010 | Goetz et al. |
| 7,988,724 B2 | 8/2011 | Salahieh et al. |
| 7,993,303 B2 | 8/2011 | Von Oepen et al. |
| 8,157,852 B2 | 4/2012 | Bloom et al. |
| 8,523,881 B2 | 9/2013 | Cabiri et al. |
| 8,647,323 B2 | 2/2014 | Guo et al. |
| 8,911,455 B2 | 12/2014 | Quadri et al. |
| 8,926,588 B2 | 1/2015 | Berthiaume et al. |
| 8,926,692 B2 | 1/2015 | Dwork |
| 9,339,378 B2 | 5/2016 | Quadri et al. |
| 9,370,423 B2 | 6/2016 | Ryan |
| 9,393,112 B2 | 7/2016 | Tuval et al. |
| 9,399,112 B2 | 7/2016 | Shevgoor et al. |
| 9,668,859 B2 | 6/2017 | Kheradvar et al. |
| 9,687,373 B2 | 6/2017 | Vad |
| 9,693,862 B2 | 7/2017 | Campbell et al. |
| 9,801,745 B2 | 10/2017 | Wubbeling et al. |
| 10,111,671 B2 | 10/2018 | Bodewadt |
| 10,117,760 B2 | 11/2018 | Mangiardi |
| 10,376,673 B2 | 8/2019 | Van Hoven et al. |
| 10,398,553 B2 | 9/2019 | Kizuka |
| 10,470,902 B2 | 11/2019 | Sheldon et al. |
| 10,646,689 B2 | 5/2020 | von Oepen et al. |
| 10,661,052 B2 | 5/2020 | McNiven et al. |
| 2001/0002445 A1 | 5/2001 | Vesely |
| 2001/0047150 A1 | 11/2001 | Chobotov |
| 2002/0013547 A1 | 1/2002 | Paskar |
| 2003/0208222 A1 | 11/2003 | Zadno-Azizi |
| 2004/0049207 A1 | 3/2004 | Goldfarb et al. |
| 2004/0064179 A1 | 4/2004 | Linder et al. |
| 2004/0116848 A1 | 6/2004 | Gardeski et al. |
| 2004/0127849 A1 | 7/2004 | Kantor |
| 2004/0133232 A1 | 7/2004 | Rosenbluth et al. |
| 2004/0147826 A1 | 7/2004 | Peterson |
| 2005/0038383 A1 | 2/2005 | Kelley et al. |
| 2005/0085903 A1 | 4/2005 | Lau |
| 2005/0137695 A1 | 6/2005 | Salahieh et al. |
| 2005/0143809 A1 | 6/2005 | Salahieh et al. |
| 2005/0256452 A1 | 11/2005 | DeMarchi et al. |
| 2005/0259452 A1 | 11/2005 | Cho |
| 2005/0283231 A1 | 11/2005 | Haug et al. |
| 2005/0277874 A1 | 12/2005 | Selkee |
| 2005/0277876 A1 | 12/2005 | Hayden |
| 2005/0288768 A1 | 12/2005 | Sowinski et al. |
| 2006/0135961 A1 | 6/2006 | Rosenman et al. |
| 2007/0060997 A1 | 3/2007 | de Boer |
| 2007/0118155 A1 | 5/2007 | Goldfarb et al. |
| 2007/0156225 A1 | 7/2007 | George et al. |
| 2007/0173757 A1 | 7/2007 | Levine et al. |
| 2007/0197858 A1 | 8/2007 | Goldfarb et al. |
| 2007/0203561 A1 | 8/2007 | Forster et al. |
| 2007/0260225 A1 | 11/2007 | Sakakine et al. |
| 2007/0270779 A1 | 11/2007 | Jacobs et al. |
| 2007/0299424 A1 | 12/2007 | Cumming et al. |
| 2008/0058722 A1 | 3/2008 | Von Oepen et al. |
| 2008/0103585 A1 | 5/2008 | Monstadt et al. |
| 2008/0109065 A1 | 5/2008 | Bowe |
| 2008/0188850 A1 | 8/2008 | Mody et al. |
| 2008/0195126 A1 | 8/2008 | Solem |
| 2008/0200980 A1* | 8/2008 | Robin ............... A61F 2/2418 623/2.11 |
| 2008/0243081 A1 | 10/2008 | Nance et al. |
| 2009/0036768 A1 | 2/2009 | Seehusen et al. |
| 2009/0069885 A1 | 3/2009 | Rahdert et al. |
| 2009/0099554 A1 | 4/2009 | Forster et al. |
| 2009/0163934 A1 | 6/2009 | Raschdorf, Jr. et al. |
| 2009/0182407 A1 | 7/2009 | Leanna et al. |
| 2009/0204005 A1 | 8/2009 | Keast et al. |
| 2009/0240326 A1 | 9/2009 | Wilson et al. |
| 2009/0276039 A1 | 11/2009 | Meretei |
| 2009/0281619 A1 | 11/2009 | Le et al. |
| 2010/0004739 A1 | 1/2010 | Vesely |
| 2010/0030057 A1 | 2/2010 | Gavriely et al. |
| 2010/0044410 A1 | 2/2010 | Argentine et al. |
| 2010/0059173 A1 | 3/2010 | Kampa et al. |
| 2010/0070009 A1 | 3/2010 | Barker |
| 2010/0082089 A1 | 4/2010 | Quadri et al. |
| 2010/0217261 A1 | 8/2010 | Watson |
| 2010/0249894 A1 | 9/2010 | Oba et al. |
| 2010/0298931 A1 | 11/2010 | Quadri et al. |
| 2010/0331776 A1 | 12/2010 | Salahieh et al. |
| 2011/0112630 A1 | 5/2011 | Groothuis et al. |
| 2011/0147251 A1 | 6/2011 | Hodshon et al. |
| 2011/0166566 A1 | 7/2011 | Gabriel |
| 2011/0166649 A1 | 7/2011 | Gross et al. |
| 2011/0202128 A1 | 8/2011 | Duffy |
| 2011/0257718 A1 | 10/2011 | Argentine |
| 2011/0307049 A1 | 12/2011 | Kao |

(56) References Cited

U.S. PATENT DOCUMENTS

| | | | |
|---|---|---|---|
| 2011/0319904 | A1 | 12/2011 | Hollett et al. |
| 2012/0022640 | A1 | 1/2012 | Gross et al. |
| 2012/0065464 | A1 | 3/2012 | Ellis et al. |
| 2012/0109078 | A1 | 5/2012 | Schaeffer |
| 2012/0172915 | A1 | 7/2012 | Fifer et al. |
| 2012/0316639 | A1 | 12/2012 | Kleinschrodt |
| 2012/0330348 | A1 | 12/2012 | Strauss et al. |
| 2012/0330408 | A1 | 12/2012 | Hillukka et al. |
| 2013/0030514 | A1 | 1/2013 | Kasprzak et al. |
| 2013/0041314 | A1 | 2/2013 | Dillon |
| 2013/0066342 | A1 | 3/2013 | Dell et al. |
| 2013/0103001 | A1 | 4/2013 | BenMaamer et al. |
| 2013/0109910 | A1 | 5/2013 | Alexander et al. |
| 2013/0110227 | A1 | 5/2013 | Quadri et al. |
| 2013/0131775 | A1 | 5/2013 | Hadley et al. |
| 2013/0289696 | A1 | 10/2013 | Maggard et al. |
| 2014/0107693 | A1 | 4/2014 | Plassman |
| 2014/0114390 | A1 | 4/2014 | Tobis et al. |
| 2014/0142688 | A1 | 5/2014 | Duffy et al. |
| 2014/0148889 | A1* | 5/2014 | Deshmukh ............. A61F 2/962 623/1.11 |
| 2014/0180124 | A1 | 6/2014 | Whiseant et al. |
| 2014/0200649 | A1 | 7/2014 | Essinger et al. |
| 2014/0228871 | A1 | 8/2014 | Cohen et al. |
| 2014/0276966 | A1 | 9/2014 | Ranucci et al. |
| 2014/0324164 | A1 | 10/2014 | Gross et al. |
| 2014/0336744 | A1 | 11/2014 | Tani et al. |
| 2014/0379074 | A1 | 12/2014 | Spence et al. |
| 2015/0005704 | A1 | 1/2015 | Heisei et al. |
| 2015/0005801 | A1 | 1/2015 | Marquis et al. |
| 2015/0073341 | A1 | 3/2015 | Salahieh et al. |
| 2015/0088189 | A1 | 3/2015 | Paul, Jr. |
| 2015/0094656 | A1 | 4/2015 | Salahieh et al. |
| 2015/0112430 | A1 | 4/2015 | Creaven et al. |
| 2015/0272759 | A1 | 10/2015 | Argentine |
| 2015/0306806 | A1 | 10/2015 | Dando et al. |
| 2016/0045311 | A1 | 2/2016 | McCann et al. |
| 2016/0074163 | A1 | 3/2016 | Yang et al. |
| 2016/0113765 | A1 | 4/2016 | Ganesan et al. |
| 2016/0128819 | A1 | 5/2016 | Giordano et al. |
| 2016/0143661 | A1 | 5/2016 | Wood et al. |
| 2017/0035566 | A1 | 2/2017 | Krone et al. |
| 2017/0042678 | A1 | 2/2017 | Ganesan et al. |
| 2017/0080186 | A1 | 3/2017 | Salahieh et al. |
| 2017/0232238 | A1 | 8/2017 | Biller et al. |
| 2018/0028177 | A1 | 2/2018 | von Oepen et al. |
| 2018/0028215 | A1 | 2/2018 | Cohen |
| 2018/0028305 | A1 | 2/2018 | von Oepen et al. |
| 2018/0028787 | A1 | 2/2018 | McNiven et al. |
| 2018/0055636 | A1 | 3/2018 | Valencia et al. |
| 2018/0055637 | A1 | 3/2018 | von Oepen et al. |
| 2018/0056033 | A1 | 3/2018 | von Oepen et al. |
| 2018/0056043 | A1 | 3/2018 | von Oepen et al. |
| 2018/0071098 | A1 | 3/2018 | Alon |
| 2018/0092744 | A1 | 4/2018 | von Oepen et al. |
| 2018/0132837 | A1 | 5/2018 | Mathen et al. |
| 2018/0133454 | A1 | 5/2018 | von Oepen et al. |
| 2018/0360457 | A1 | 12/2018 | Ellis et al. |
| 2019/0015086 | A1 | 1/2019 | Blumenthal |
| 2019/0030285 | A1 | 1/2019 | Prabhu et al. |
| 2019/0274831 | A1 | 9/2019 | Prabhu |
| 2020/0155804 | A1 | 5/2020 | von Oepen et al. |
| 2020/0230352 | A1 | 7/2020 | Mcniven et al. |

FOREIGN PATENT DOCUMENTS

| | | | |
|---|---|---|---|
| CN | 1859942 | A | 11/2006 |
| CN | 1961983 | A | 5/2007 |
| CN | 101247847 | A | 8/2008 |
| CN | 101426452 | A | 5/2009 |
| CN | 101479006 | A | 7/2009 |
| CN | 101506538 | A | 8/2009 |
| CN | 102159277 | A | 8/2011 |
| CN | 102258402 | A | 11/2011 |
| CN | 102405022 | A | 4/2012 |
| CN | 102481433 | A | 5/2012 |
| CN | 102548505 | A | 7/2012 |
| CN | 102770080 | | 11/2012 |
| CN | 102933161 | A | 2/2013 |
| CN | 103517689 | A | 1/2014 |
| CN | 103702635 | A | 4/2014 |
| CN | 103841899 | | 6/2014 |
| CN | 103957993 | A | 7/2014 |
| CN | 104203329 | A | 12/2014 |
| CN | 104812439 | A | 7/2015 |
| CN | 105246434 | A | 1/2016 |
| CN | 105899167 | A | 8/2016 |
| EP | 0989882 | A1 | 4/2000 |
| EP | 1980288 | | 10/2008 |
| EP | 2537487 | | 12/2012 |
| EP | 2702965 | | 3/2014 |
| EP | 3009103 | | 4/2016 |
| JP | 06-343702 | A | 12/1994 |
| JP | 2003062072 | | 3/2003 |
| JP | 2006528911 | | 12/2006 |
| JP | 2013516244 | | 5/2013 |
| WO | WO 2001051114 | | 7/2001 |
| WO | WO 2007044285 | | 4/2007 |
| WO | WO 2007136829 | | 11/2007 |
| WO | WO 2008103722 | | 8/2008 |
| WO | WO 2010024801 | | 3/2010 |
| WO | WO 2010121076 | | 10/2010 |
| WO | 2011/033783 | A1 | 3/2011 |
| WO | WO 2012020521 | | 2/2012 |
| WO | 2012/057983 | A1 | 5/2012 |
| WO | WO 2012151396 | | 11/2012 |
| WO | 2013/126529 | A2 | 8/2013 |
| WO | WO 2014064694 | | 5/2014 |
| WO | WO 2014121280 | | 8/2014 |
| WO | WO 2014128705 | | 8/2014 |
| WO | WO 2015191938 | | 12/2015 |
| WO | WO 2016022797 | | 2/2016 |
| WO | WO 2016112085 | | 7/2016 |
| WO | WO 2016144708 | | 9/2016 |
| WO | WO 2016150806 | | 9/2016 |
| WO | WO 2016183526 | | 11/2016 |
| WO | 2017/023534 | A2 | 2/2017 |
| WO | WO 2018023038 | | 2/2018 |
| WO | WO 2018023043 | | 2/2018 |
| WO | WO 2018023044 | | 2/2018 |
| WO | WO 2018023045 | | 2/2018 |
| WO | WO 2018023052 | | 2/2018 |
| WO | WO 2018044446 | | 3/2018 |
| WO | WO 2018044447 | | 3/2018 |
| WO | WO 2018044448 | | 3/2018 |
| WO | WO 2018044449 | | 3/2018 |
| WO | WO 2018067788 | | 4/2018 |
| WO | WO 2018093426 | | 5/2018 |

OTHER PUBLICATIONS

U.S. Appl. No. 15/662,001, filed Jun. 20, 2019, Office Action.
U.S. Appl. No. 15/662,001, filed Oct. 4, 2019, Office Action.
U.S. Appl. No. 15/662,001, filed Dec. 18, 2019, Notice of Allowance.
U.S. Appl. No. 15/662,001, filed Mar. 24, 2020, Notice of Allowance.
U.S. Appl. No. 15/662,008, filed Sep. 13, 2019, Office Action.
U.S. Appl. No. 15/662,008, filed Jan. 31, 2020, Notice of Allowance.
U.S. Appl. No. 15/662,013, filed Jun. 13, 2019, Office Action.
U.S. Appl. No. 15/662,013, filed Oct. 10, 2019, Office Action.
U.S. Appl. No. 15/662,013, filed Dec. 5, 2019, Advisory Action.
U.S. Appl. No. 15/662,013, filed May 7, 2020, Notice of Allowance.
U.S. Appl. No. 15/662,014, filed May 31, 2019, Office Action.
U.S. Appl. No. 15/662,014, filed Oct. 2, 2019, Notice of Allowance.
U.S. Appl. No. 15/662,066, filed Jul. 11, 2019, Office Action.
U.S. Appl. No. 15/662,066, filed Dec. 16, 2019, Office Action.
U.S. Appl. No. 15/662,066, filed Feb. 27, 2020, Advisory Action.
U.S. Appl. No. 15/662,076, filed Oct. 8, 2019, Notice of Allowance.

(56) References Cited

OTHER PUBLICATIONS

U.S. Appl. No. 15/662,076, filed Jan. 31, 2020, Notice of Allowance.
U.S. Appl. No. 15/662,089, filed Oct. 7, 2019, Office Action.
U.S. Appl. No. 15/662,089, filed Jan. 10, 2020, Office Action.
U.S. Appl. No. 15/662,093, filed Mar. 7, 2019, Office Action.
U.S. Appl. No. 15/662,093, filed Aug. 29, 2019, Office Action.
U.S. Appl. No. 15/662,093, filed Dec. 3, 2019, Office Action.
U.S. Appl. No. 15/662,093, filed May 6, 2020, Office Action.
U.S. Appl. No. 15/662,098, filed Jul. 5, 2019, Office Action.
U.S. Appl. No. 15/662,098, filed Jan. 27, 2020, Office Action.
U.S. Appl. No. 15/662,098, filed Mar. 23, 2020, Advisory Action.
U.S. Appl. No. 15/662,098, filed Apr. 30, 2020, Office Action.
U.S. Appl. No. 15/662,142, filed Dec. 20, 2019, Advisory Action.
U.S. Appl. No. 15/662,142, filed Apr. 17, 2020, Office Action.
U.S. Appl. No. 15/724,499, filed Jul. 15, 2019, Notice of Allowance.
U.S. Appl. No. 15/724,499, filed Aug. 27, 2019, Notice of Allowance.
U.S. Appl. No. 15/724,499, filed Nov. 22, 2019, Notice of Allowance.
U.S. Appl. No. 15/724,499, filed Mar. 25, 2020, Office Action.
Advisory Action received for U.S. Appl. No. 15/662,093, dated Jul. 9, 2020.
Notice of Allowance received for U.S. Appl. No. 15/724,499, dated Jul. 1, 2020.
Office Action received for U.S. Appl. No. 15/662,066, dated May 21, 2020.
Office Action received for U.S. Appl. No. 15/662,089, dated Jun. 11, 2020.

* cited by examiner

MECHANICAL INTERLOCK FOR CATHETERS

CROSS-REFERENCE TO RELATED APPLICATIONS

This application is a divisional of U.S. patent application Ser. No. 15/662,076, filed Jul. 27, 2017, which claims benefit of and priority to U.S. Provisional Patent Application No. 62/368,711, filed Jul. 29, 2016 and titled "Hypotube Reinforced Intravascular Device Delivery Systems and Methods", U.S. Provisional Patent Application No. 62/380,246, filed Aug. 26, 2016 and titled "Rotational Fixation of Catheters", U.S. Provisional Patent Application No. 62/436,887, filed Dec. 20, 2016 and titled "Mechanical Interlock for of Catheters", U.S. Provisional Patent Application No. 62/462,776, filed Feb. 23, 2017 and titled "Systems and Methods for Loading and Deploying an Intravascular Device," the disclosures of which are incorporated herein by references in their entireties.

BACKGROUND OF THE DISCLOSURE

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. The distal end of the catheter may be deflected by one or more wires positioned inside the catheter. Precise control of the distal end of the catheter allows for more reliable and faster positioning of a medical device and/or implant and other improvements in the procedures.

The devices can also be directed through the valve chordae or papillary muscles, for example, for interventional therapy to the mitral valve. When such procedures require the use of more than one instrument, each instrument would be dependent upon proper positioning in relation to the valve. Therefore, positioning or steering mechanisms need to be built into each instrument. This adds further cost, complexity, and time to the procedures.

Other procedures may include tracking a catheter and/or access sheath from a puncture in the femoral vein through the intra-atrial septum to the left atrium. This pathway may be used to access the left atrium for ablation of the atrium wall or ablation around the pulmonary veins. Such interventional therapies would require precise alignment with target areas for proper ablation placement. Additionally, alternative access routes and/or access routes to other cavities may be desired.

In particular, a smaller thickness of the elongated portion of the intravascular device delivery system allows access routes to be used that may have previously been too small in diameter and/or reduce the likelihood of trauma in conventional access routes through the patient's vasculature. A smaller thickness of the elongated portion also reduces the force necessary to move the delivery system to the target location. A smaller thickness of the elongated portion also allows more robust steering mechanisms to be used to direct or steer the catheter and/or access sheath to the target location.

BRIEF SUMMARY OF THE DISCLOSURE

In an embodiment, an intravascular device delivery system includes an elongated member. The elongated member includes at least one steerable catheter and a flexible hypotube positioned radially outside and circumferentially about the at least one steerable catheter. The at least one steerable catheter has a proximal end, a distal end, and a longitudinal axis extending therebetween. The flexible hypotube is coaxial with the at least one steerable catheter and has at least one slit cut and may have an additional island cuts out to direct flexibility of the flexible hypotube. The flexible hypotube and the at least one steerable catheter are rotationally fixed to one another at a first key assembly.

In another embodiment, an intravascular device delivery system includes a handle and an elongated member operably coupled to the handle. The elongated member includes at least one steerable catheter and a flexible hypotube positioned radially outside and circumferentially about the steerable catheter. The at least one steerable catheter has a proximal end, a distal end, and a longitudinal axis extending therebetween. The flexible hypotube is coaxial with the at least one steerable catheter and has at least one island cut and at least one slit cut to direct flexibility of the flexible hypotube. The flexible hypotube and the at least one steerable catheter are rotationally fixed to one another at a first key assembly. The handle has one or more controls thereon to move the at least one steerable catheter longitudinally relative to the flexible hypotube.

In yet another embodiment, a method for delivering an intravascular device includes steering a steerable catheter in a first plane, the steerable catheter being positioned radially inside a flexible hypotube; and bending the flexible hypotube in the first plane to create a first bend in the flexible hypotube. The method also includes advancing the steerable catheter distally relative to the flexible hypotube and distal of a distal end of the flexible hypotube, steering the steerable catheter in a second plane, and positioning a distal end of the steerable catheter at a target location.

In yet another embodiment, an intravascular device delivery system includes a catheter having a flexible hypotube including a first hypotube of a first stiffness and a second hypotube of a second stiffness. The first hypotube and the second hypotube are joined together through a mechanical interlock. The first and second hypotubes being covered with an outer sheath.

In yet another embodiment, an intravascular delivery device system includes a catheter including a first hypotube having a first stiffness portion and a second stiffness portion that is stiffer than the first stiffness portion. A stiffening member is disposed within a portion of the catheter and is movable relative to the first stiffness portion and the second stiffness portion. Movement of the stiffening member from the first stiffness portion to the second stiffness portion changes the flexibility of the first stiffness portion to allow enhanced flexibility.

This summary is provided to introduce a selection of concepts that are further described below in the detailed description. This summary is not intended to identify specific features of the claimed subject matter, nor is it intended to be used as an aid in limiting the scope of the claimed subject matter.

Additional features of embodiments of the disclosure will be set forth in the description which follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

Figure 1:
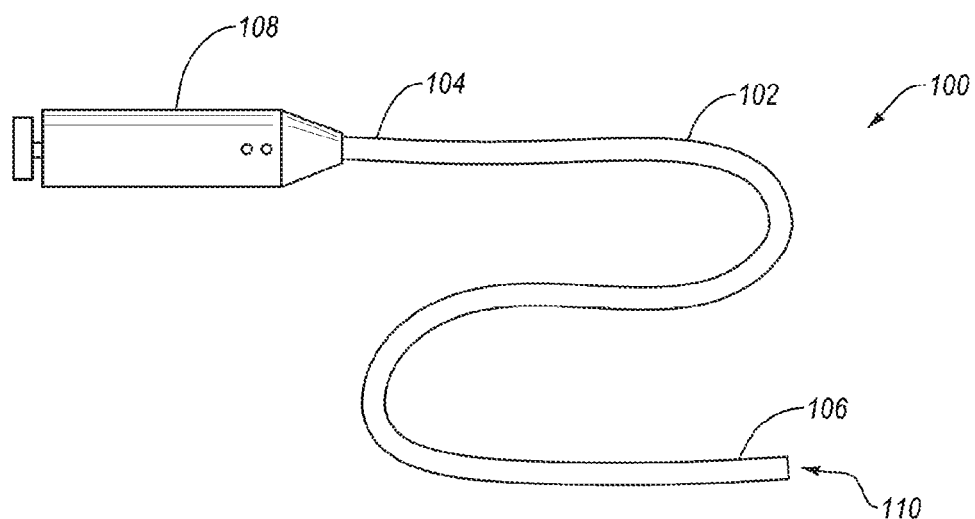
FIG. 1 is a schematic representation of an embodiment of an intravascular device delivery system, according to the present disclosure.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to manufacturing and using intravascular device delivery systems or other steerable intravascular system. An intravascular device delivery system may allow a medical professional to deliver an intravascular or other medical device to a target location in a patient's body. While the present disclosure will describe intravascular device delivery systems and applications thereof in relation to intravascular procedures in the heart, it should be understood that the devices, systems, and methods described herein may be applicable to other bodily lumens and/or cavities. Additionally, elements described in relation to any embodiment depicted and/or described herein may be combinable with elements described in relation to any other embodiment depicted and/or described herein. For example, and not by way of limitation to any other combinations of embodiments, any element described in relation to an embodiment depicted in FIG. 2 may be combinable with any element of an embodiment described in FIG. 4, and any element described in relation to an embodiment described in FIG. 5 may be combinable with any element of an embodiment depicted in FIG. 3, any element described in relation to an embodiment described in FIG. 10 may be combinable with any element of an embodiment depicted in FIG. 7, any element described in relation to an embodiment described in FIGS. 8-9 may be combinable with any element of an embodiment depicted in FIGS. 2-7 and 10, and any element described in relation to an embodiment described in FIGS. 11-14 may be combinable with any elements of an embodiment depicted in FIGS. 2-10.

An intravascular device delivery system may include a flexible elongated member that has a distal end and a proximal end. A handle may be connected to a proximal end of the elongated member to allow a user, such as a medical professional and/or clinician, to control one or more movements of the elongated member. An intravascular device may be positioned at and/or connected to the distal end of the elongated member.

In some embodiments, the elongated member may include a plurality of elements. For example, the elongated member may include a plurality of elements that extend from the proximal end to the distal end. In some embodiments, at least one of the elements of the elongated member may include a plurality of lumens therethrough to allow steerability of the element. In at least one embodiment, at least one element of the elongated member may be steerable in at least two planes.

In some embodiments, the handle may include one or more controls (e.g., a knob, a button, a lever, or other controls) that may move at least one part of the intravascular device delivery system relative to another. For example, the handle may include one or more controls for moving at least one element of the elongated member relative to another element of the elongated member. The handle may move an inner element relative to an outer element of the elongated member in a proximal direction, in a distal direction, in a rotational direction, or combinations thereof.

FIG. 1 illustrates a schematic representation of an intravascular device delivery system 100. The system 100 may include an elongated member 102 having a proximal end 104 and a distal end 106. A handle 108 may be connected to the proximal end 104 of the elongated member 102. An intravascular device 110 may be positioned at and/or connected to the distal end 106.

The elongated member 102 may be flexible, allowing the elongated member 102 to traverse a patient's tortuous vasculature or other anatomy. In some embodiments, the elongated member 102 may deliver the intravascular device 110 to a target location in the patient's body, such as delivering a filter, scaffold, stent, body tissue repair device, heart valve, or other implantable devices. In other embodiments, the system 100 and elongated member 102 may be provided without an intravascular device 110 at the distal end 106 such that the system may recapture, reposition, or otherwise move an intravascular device previously positioned in the patient's body.

The elongated member 102 of the system 100 may include one or more elements therein. An element of the elongated member 102 may include a catheter, a guidewire, a sheath, a drive cable, other tubular and/or solid element, or combinations thereof. In some embodiments an element of the elongated member 102 may extend an entire length of the elongated member 102 from a proximal end 104 to a distal end 106 of the elongated member 102. In other embodiments, an element of the elongated member 102 may have a length less than the entire length of the elongated member 102. For example, an element may provide support to the elongated member 102 from the proximal end 104 toward the distal end 106 without continuing the entire length to the distal end 106.

Figure 2:
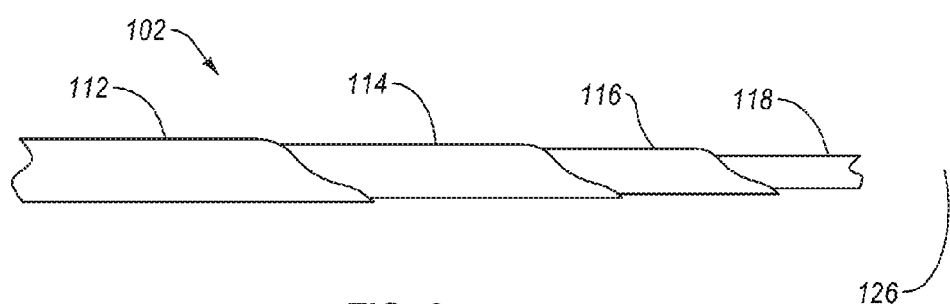
FIG. 2 is a side partial cutaway view illustrating an embodiment of the elements of the elongated member of FIG. 1, according to the present disclosure.

FIG. 2 is a side partial cutaway view of part of an embodiment of the elongated member 102 of the intravascular device delivery system 100 of FIG. 1. In some embodiments, the elongated member 102 may include an outer sleeve 112, a flexible hypotube 114, a steerable catheter 116, and an inner catheter 118. In some embodiment, the inner element may be an inner catheter. In other embodiments, the inner element 118 may be a guidewire or other guide element to assist in directing the elongated member 102 through tortuous anatomy. In some embodiments, the flexible hypotube may be a lasercut hypotube, a hydrocut hypotube, a hypotube with one or more cuts therein by other cutting methods, such as EDM or mechanical cutting, or a 3D printed hypotube with one or more openings therein.

The elongated member 102 has a longitudinal axis 126 that extends from the proximal end (i.e., proximal end 104 in FIG. 1) to the distal end (i.e., distal end 106 in FIG. 1) of the elongated member 102. In some embodiments, all of the elements of the elongated member 102 may extend a full length of the elongated member 102. In other embodiments, at least one of the elements may have a length that is less than the full length of the elongated member 102. For example, the flexible hypotube 114 may have a length that is less than the full length of the elongated member 102. In other examples, the outer sleeve 112 may have a length less than the full length of the elongated member 102. In at least one example, the flexible hypotube 114 may have a length that is less than a length of the steerable catheter 116.

In some embodiments, the flexible hypotube 114 may have a wall thickness that is less than the thickness of a conventional steerable catheter. For example, the flexible hypotube 114 may have a wall thickness that is a percentage of a wall thickness of the steerable catheter 116 in a range having upper value, a lower value, or upper and lower values including any of 10%, 15%, 20%, 25%, 30%, 35%, 40%, 45%, 50%, 60%, 70%, 80%, 90% or any values therebetween. For example, the wall thickness of the flexible hypotube 114 may be less than 90% of the wall thickness of the steerable catheter 116. In other examples, the wall thickness of the flexible hypotube 114 may be between 10% and 90% of the wall thickness of the steerable catheter 116. In yet other examples, the wall thickness of the flexible hypotube 114 may be between 15% and 50% of the wall thickness of the steerable catheter 116. In at least one embodiment, the wall thickness of the flexible hypotube 114 may be about 20% of the wall thickness of the steerable catheter 116.

Figure 3:
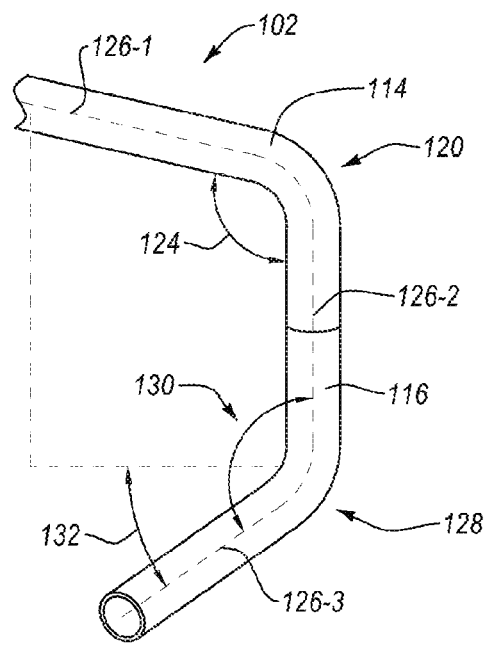
FIG. 3 is a perspective view of the embodiment of an elongated member of FIG. 2 traversing the compound bends used to access the mitral valve of the heart, according to the present disclosure.

FIG. 3 illustrates an example of a series of compound bends that the elongated member 102 may perform during the delivery, repair, recapture, repositioning, or other interaction with an intravascular device at a mitral valve in a patient's heart. While embodiments of an intravascular device and intravascular device delivery system are described herein in relation to mitral valve repair, it should be understood that embodiments of the present disclosure may be used in other intravascular procedures, such as septal repair, transapical procedures, transeptal procedures, transarterial procedures, other coronary procedures, other intravascular procedures, or other intraluminal medical procedures.

While accessing a mitral valve or other intravascular procedure having at least one bend in a bodily cavity, the elongated member 102 may be steered by the steerable catheter 116. The steerable catheter 116 may be any suitable steerable catheter 116 known in the art. In some embodiments, the steerable catheter 116 may be steerable in at least one plane of motion. In another embodiment, the steerable catheter 116 may be steerable in at least two planes of motion. In at least one embodiment, the steerable catheter 116 is steerable in two planes of motion substantially perpendicular to one another.

In the depicted embodiment, the elongated member 102 is shown with only the flexible hypotube 114 and the steerable catheter 116 for clarity. The steerable catheter 116 may extend distally at least partially from a distal end of the flexible hypotube 114. The elongated member 102 has a first bend 120 in which both the flexible hypotube 114 and the steerable catheter 116 deflect. The first bend 120 may have a first bend angle 124 measured between a first longitudinal axis 126-1 proximal of the first bend 120 to a second longitudinal axis 126-2 distal the first bend 120. In some embodiments, the first bend angle 124 may be in a range having an upper value, a lower value, or an upper and lower value including any of 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, or any values therebetween. For example, the first bend angle 124 may be greater than 60°. In other example, the first bend angle 124 may be less than 175°. In yet other examples, the first bend angle 124 may be in a range of 60° to 175°. In further examples, the first bend angle 124 may be in a range of 90° to 120°. In at least one example, the first bend angle 124 may be about 105°.

The elongated member 102 has a second bend 128 in which the steerable catheter 116 is deflected with a compound angle relative to the first longitudinal axis 126-1. The second bend 128 has a second bend angle 130 between a third longitudinal axis 126-3 distal of the second bend 128 relative to the second longitudinal axis 126-2 proximal the second bend 128. The second bend 128 may also have a rotational angle 132 relative to a plane in which the first longitudinal axis 126-1 and the second longitudinal axis 126-2 lie. In other words, the rotational angle 132 is relative to the amount of rotation of the third longitudinal axis 126-3 relative to the direction of the first bend 120.

In some embodiments, the second bend angle 130 may be in a range having an upper value, a lower value, or an upper and lower value including any of 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, or any values therebetween. For example, the second bend angle 130 may be greater than 60°. In other example, the second bend angle 130 may be less than 175°. In yet other examples, the second bend angle 130 may be in a range of 60° to 175°. In further examples, the second bend angle 130 may be in a range of 80° to 110°. In at least one example, the second bend angle 130 may be about 90°.

In some embodiments, the rotational angle 132 of the third longitudinal axis 126-3 (i.e., a distal end of the steerable catheter 116) relative to the first longitudinal axis 126-1 may be in a range having an upper value, a lower value, or an upper and lower value including any of 30°, 35°, 40°, 45°, 50°, 55°, 60°, 65°, 70°, 75°, 80°, 85°, 90°, 100°, 110°, 120°, 130°, 140°, 150°, 160°, or any values therebetween. For example, the rotational angle 132 may be greater than 30°. In other example, the rotational angle 132 may be less than 160°. In yet other examples, the rotational angle 132 may be in a range of 30° to 160°. In further examples, the rotational angle 132 may be in a range of 45° to 135°. In at least one example, the second bend angle 130 may be about 60°.

Figure 4A:
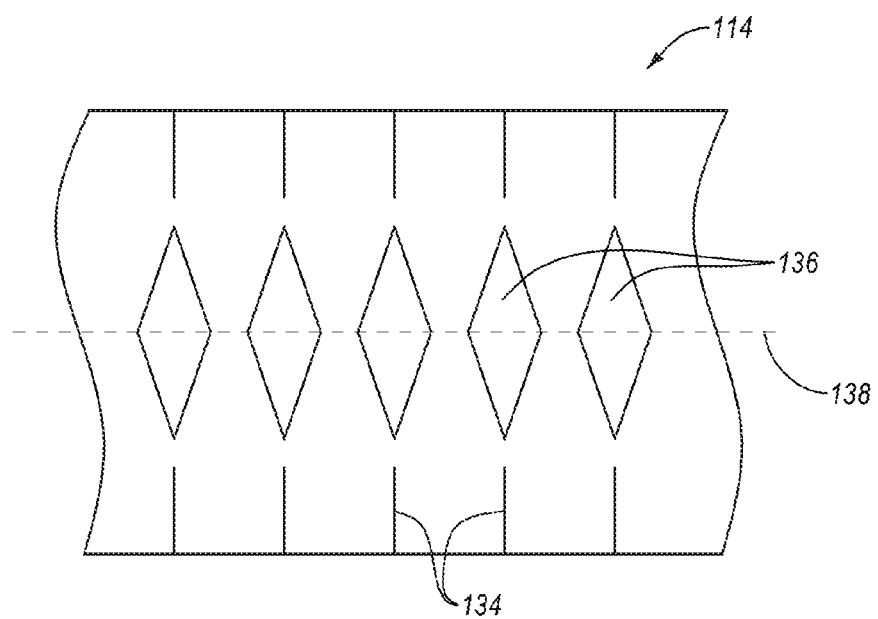
FIG. 4A is a plan view of an embodiment of a cut pattern in a flexible hypotube, according to the present disclosure.

In order to allow the flexible hypotube 114 to bend with the steerable catheter 116, one or more cuts may be made in through a wall of the flexible hypotube 114. FIG. 4A illustrates a flat view of a cut pattern for a flexible hypotube 114 according to the present disclosure. The flat view illustrates the pattern of the cuts as though a cylindrical hypotube were laid flat. In other words, the top edge of the cut pattern and the bottom edge of the cut pattern are connected and continuous in the flexible hypotube 114 such that the slits 134 and island cuts 136 are oriented circumferential and spaced apart by the spines therebetween. The cut pattern may include at least one slit 134 and at least one island cut 136. As shown in FIG. 4A, the cut pattern may have a plurality of slits 134 and/or a plurality of island cuts 136.

The slit 134 may transmit longitudinal force along the flexible hypotube 114 and allow expansion of the flexible hypotube 114 when the flexible hypotube 114 is deflected in a direction opposite the slit 134. The island cuts 136 may allow compression of the flexible hypotube 114 when the flexible hypotube 114 is deflected in a direction of the island cuts 136. For example, slits 134 and island cuts 136 located rotationally opposite one another on a flexible hypotube 114 may direct preferential bending of the hypotube along a center line 138 of the island cuts 136. For example, a flexible hypotube 114 with the cut pattern of FIG. 4A may preferentially bend along the center line 138 within a bend region defined by the cut pattern.

While the island cuts 136 are depicted in FIG. 4A as diamond-shaped, the island cuts 136 may have one or more other shapes, such as square, rhombohedral, triangular, rectangular, circular, oblong, other elliptical, other polygonal, irregular, or combinations thereof.

Figure 4B:
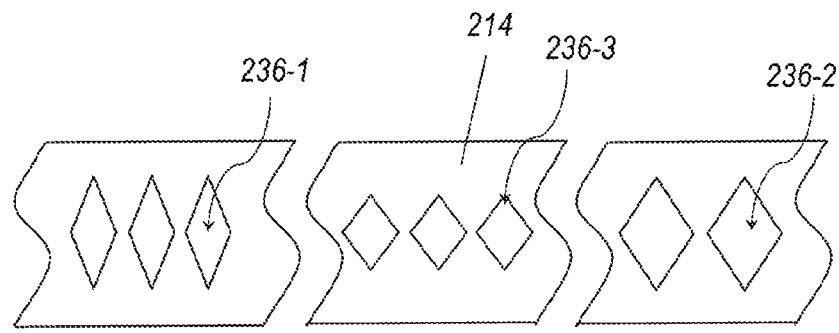
FIG. 4B is a side schematic view of an embodiment of a flexible hypotube with island cuts of varying sizes, according to the present disclosure.

FIG. 4B is a side view of a flexible hypotube 214 having a plurality of island cuts 236 therein which may vary in size along a longitudinal length of the flexible hypotube 214. For example, a first island cut 236-1 may be shorter in the longitudinal direction than a second island cut 236-2 in a different longitudinal portion of the flexible hypotube 214. In at least one embodiment, the island cuts increase in longitudinal length in a distal direction. In another example, a third island cut 236-3 may be narrower in the rotational direction about the flexible hypotube 214 than the second island cut 236-2 in a different longitudinal portion of the flexible hypotube 214. In at least one embodiment, the island cuts become wider in the rotation direction in a distal direction. The flexible hypotube 214 may have one or more slits opposite the island cuts 236 (not visible in FIG. 4B).

Figure 5A:
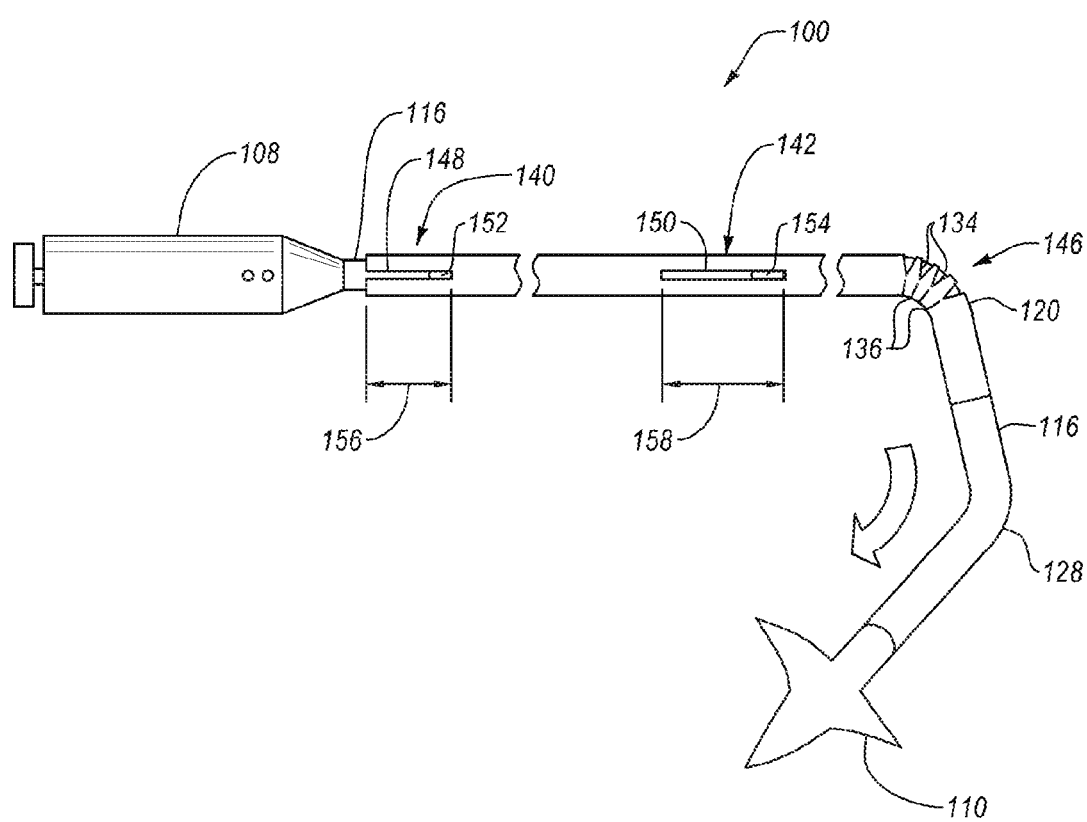
FIG. 5A is a schematic representation of the embodiment of an intravascular device delivery system of FIG. 1 showing a keyed hypotube, according to the present disclosure.

FIG. 5A illustrates the preferential bending of the flexible hypotube 114 in the intravascular device delivery system 100. Only the flexible hypotube 114 and steerable catheter 116 of the elongated member are shown in FIG. 5 for clarity and to show the relative motion of the flexible hypotube 114 and steerable catheter 116.

The flexible hypotube 114 has a bend region 146 containing one or more slits 134 and island cuts 136. The steerable catheter 116 may apply a transverse force to the flexible hypotube 114 to bend the bend region 146. As shown in FIG. 5, the slits 134 may open (i.e., expand) and the island cuts 136 may close (i.e., compress) to allow the bend region 146 to bend at the first bend 120. The orientation of the first bend 120 (i.e. rotational orientation about a longitudinal axis) may be controlled by rotation of the steerable catheter 116 and flexible hypotube 114 together.

The flexible hypotube 114 and steerable catheter 116 may be rotationally fixed relative to one another in one or more key assemblies. In the embodiment shown in FIG. 5A, the flexible hypotube 114 and steerable catheter 116 are rotationally fixed relative to one another by a first key assembly 140 and a second key assembly 142. In other embodiments, the flexible hypotube 114 and the steerable catheter 116 may be rotationally fixed relative to one another by one key assembly. In yet other embodiments, the flexible hypotube 114 and the steerable catheter 116 may be rotationally fixed relative to one another by three or more key assemblies positioned longitudinally along the flexible hypotube 114 and the steerable catheter 116. In further embodiments, the flexible hypotube 114 and steerable catheter 116 may be rotationally fixed relative to one another by a first key assembly 140 that extends an entire longitudinal length of the flexible hypotube 114 or steerable catheter 116.

The first key assembly 140 may rotationally fix the flexible hypotube 114 and the steerable catheter 116 by a mechanical interlock of one or more elements between the flexible hypotube 114 and the steerable catheter 116. For example, the flexible hypotube 114 includes a first slot 148 and a second slot 150. The first slot 148 and the second slot 150 are configured to receive a first tab 152 and a second tab 154 of the steerable catheter 116, such that the first tab 152 engages with the first slot 148 to form the first key assembly 140 and the second tab 154 engages with the second slot 150 to form the second key assembly 142. In other embodiments, the mechanical interlock may have other forms. For example, the first slot 148 may be located in the steerable catheter 116 and the first tab 152 may be fixed relative to the flexible hypotube. In other examples, such as a first key assembly 140 that extends an entire longitudinal length of the flexible hypotube 114 or steerable catheter 116, the first slot 148 may extend substantially or the entire longitudinal length of the flexible hypotube 114 or steerable catheter 116 and a plurality of tabs (e.g., first tab 152 and second tab 154) may engage with the first slot 148.

In some embodiments, the first tab 152 and/or second tab 154 may be integrally formed with the steerable catheter 116. However, an integrally formed first tab 152 and/or second tab 154 may introduce challenges during assembly of the device. In other embodiments, a first tab 152 and/or second tab 154 may be connected to the steerable catheter 116 through the first slot 148 and/or second slot 150, respectively, after the steerable catheter 116 is positioned radially within the flexible hypotube 114. For example, a first tab 152 and/or second tab 154 may be connected to an outer surface of the steerable catheter 116 by sonic welding, thermal welding, an adhesive, a clip, a pin, a rivet, a screw, another mechanical fastener, or a combination thereof.

Figure 5B:
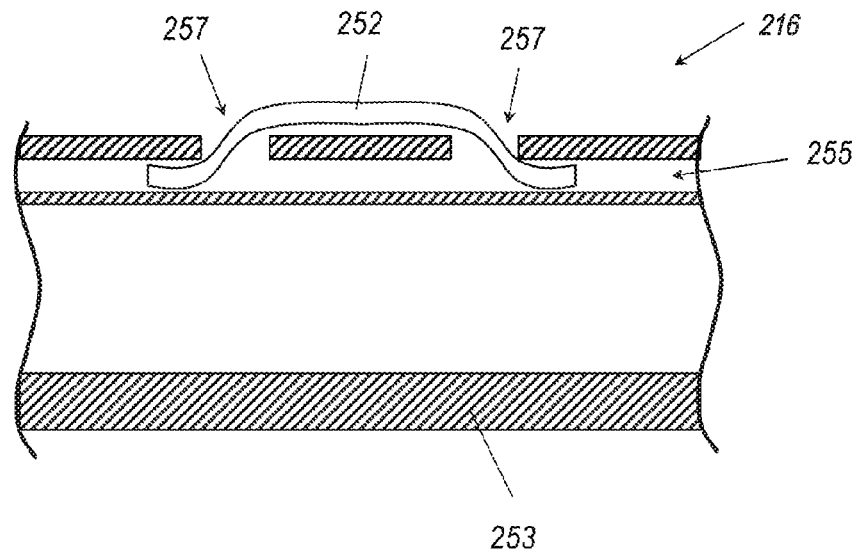
FIG. 5B is a cross-sectional view of an embodiment of a steerable catheter with a tab keyed to the flexible hypotube, according to the present disclosure.

FIG. 5B is a longitudinal cross-sectional of an embodiment of a steerable catheter 216 with a tab 252. The steerable catheter 216 has a body 253. The body 253 includes a lumen 255 contained within a wall of the body 253 that extends along a least a portion of the longitudinal length of the steerable catheter 216. One or more cuts 257 are made in the outer surface of the body 253 through to the lumen 255. A tab 252 is inserted into the one or more cuts 257 to retain the tab 252 in the body 253 of the steerable catheter 216 with at least a portion of the tab 252 extending radially from the body 253, as shown in FIG. 5B. The tab 252 may include or be made of spring steel, shape memory material like Nitinol, other steel alloys, aluminum, titanium, an organic polymer, an inorganic polymer, other materials, or combinations thereof. In some embodiments, the tab 252 is held in the lumen 255 with an adhesive.

In other embodiments, the tab 252 is placed in the steerable catheter 216 before positioning the steerable catheter 216 in the flexible hypotube. In such embodiments, the tab 252 is held in the lumen 255 with an adhesive at only one end of the tab 252, allowing the other end to move freely. The free end allows the tab to collapse radially during positioning of the steerable catheter 216 in the flexible hypotube.

Figure 5C:
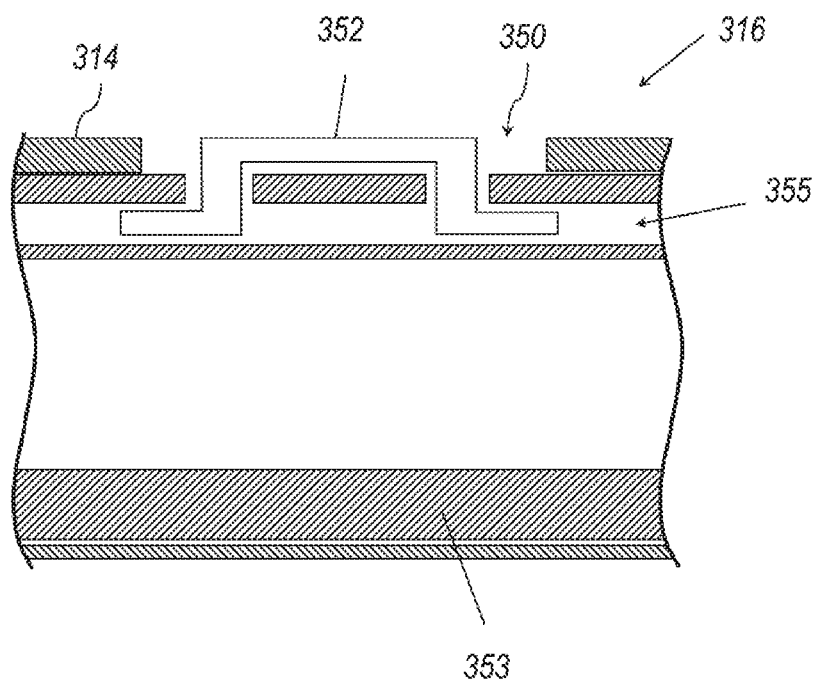
FIG. 5C is a cross-sectional view of another embodiment of a steerable catheter with a tab keyed to a flexible hypotube, according to the present disclosure.

As shown in FIG. 5C, in other embodiments of a steerable catheter 316, the tab 352 may have other shapes than shown in FIG. 5B. For example, the tab 352 may have discontinuous corners, such as 90° corners. In other embodiments, the tab 352 may have a mix of curved surfaces and discontinuous corners to facilitate assembly of the tab 352 into the body 353 of the steerable catheter 316 through the slot 350 of the flexible hypotube 314 while allowing for 1:1 torque transmission between the steerable catheter 316 and the flexible hypotube 314.

Referring again to FIG. 5A, the first key assembly 140 rotationally keys the flexible hypotube to the steerable catheter 116 by limiting and/or preventing movement of the first tab 152 rotationally relative to the first slot 148. The second key assembly 142 rotationally keys the flexible hypotube 114 to the steerable catheter 116 at a location distal of the first key assembly 140 by limiting and/or preventing movement of the second tab 154 rotationally relative to the second slot 150. The first slot 148 has a first slot length 156 in a longitudinal direction. The first tab 152 may move longitudinally within the first slot 148, allowing at least a portion of the steerable catheter 116 to translate longitudinally relative to the flexible hypotube 114 while the steerable catheter 116 is rotationally keyed to the flexible hypotube 114. The second tab 154 may move longitudinally within the second slot 150, allowing at least another portion of the steerable catheter 116 (distal of the first key assembly 140) to translate longitudinally relative to the flexible hypotube 114.

Longitudinal translation of the steerable catheter 116 relative to the flexible hypotube 114 allows the steerable catheter 116 to bend the bend region 146 of the flexible hypotube 114 at the first bend 120, and then translate longitudinally in a distal direction and project from the flexible hypotube 114 (i.e., extend beyond a distal end of the flexible hypotube 114). For example, the steerable catheter 116 may bend the flexible hypotube 114 at the bend region 146 in a first direction and move distally through the flexible hypotube 114 beyond the distal end of the flexible hypotube 114. The steerable catheter 116 may then be steered in a second direction by one or more controls on the handle 108. The amount of longitudinally displacement of the steerable catheter 116 relative to the flexible hypotube 114 may be at least partially determined by the first slot length 156 and/or the second slot length 158.

In some embodiments, the first slot length 156 may be equivalent to the second slot length 158. In other embodiments, the first slot length 156 may be greater than the second slot length 158. In yet other embodiments, the first slot length 156 may be less than the second slot length 158. In some embodiments, the first slot length 156 and/or the second slot length 158 may be in a range including an upper value, a lower value, or upper and lower values including any of 2.0 centimeters, 2.5 centimeters, 3.0 centimeters, 3.5 centimeters, 4.0 centimeters, 4.5 centimeters, 5.0 centimeters, 5.5 centimeters, 6.0 centimeters, 6.5 centimeters, 7.0 centimeters, 7.5 centimeters, 8.0 centimeters, 8.5 centimeters, 9.0 centimeters, 9.5 centimeters, 10.0 centimeters, or any values therebetween. For example, the first slot length 156 and/or the second slot length 158 may be greater than 2.0 centimeters. In another example, the first slot length 156 and/or the second slot length 158 may be less than 10.0 centimeters. In yet other examples, the first slot length 156 and/or the second slot length 158 may be between 2.0 centimeters and 5.0 centimeters. In further examples, the first slot length 156 and/or the second slot length 158 may be in a range of 2.5 centimeters to 4.5 centimeters. In at least one embodiment, the first slot length 156 and/or the second slot length 158 may be about 3.0 centimeters.

The first slot 148 and the second slot 150 are rotationally aligned with one another in the embodiment of FIG. 5A. In other embodiments, the first slot 148 and second slot 150 may be rotationally displaced from one another. For example, the first slot 148 may be on a first side of the flexible hypotube 114 and the second slot 150 may be displaced at an angular amount from the first slot 148, such as 180° to angularly oppose the first slot 148. In other examples, the first slot 148 and second slot 150 may be rotationally displaced from one another by another angle between 0° and 180°.

In some embodiments the first slot length 156 and/or second slot length 158 may limit the amount the steerable catheter 116 may extend distally of a distal end of the flexible hypotube 114. For example, the amount the steerable catheter 116 may extend distally of a distal end of the flexible hypotube 114 may be in a range including an upper value, a lower value, or upper and lower values including any of 2.0 centimeters, 2.5 centimeters, 3.0 centimeters, 3.5 centimeters, 4.0 centimeters, 4.5 centimeters, 5.0 centimeters, 5.5 centimeters, 6.0 centimeters, 6.5 centimeters, 7.0 centimeters, 7.5 centimeters, 8.0 centimeters, 8.5 centimeters, 9.0 centimeters, 9.5 centimeters, 10.0 centimeters or any values therebetween. For example, the amount the steerable catheter 116 may extend distally of a distal end of the flexible hypotube 114 may be greater than 2.0 centimeters. In another example, the amount the steerable catheter 116 may extend distally of a distal end of the flexible hypotube 114 may be less than 10.0 centimeters. In yet other examples, the amount the steerable catheter 116 may extend distally of a distal end of the flexible hypotube 114 may be between 2.0 centimeters and 10.0 centimeters. In further examples, the amount the steerable catheter 116 may extend distally of a distal end of the flexible hypotube 114 may be in a range of 2.5 centimeters to 6.5 centimeters. In at least one embodiment, the amount the steerable catheter 116 may extend distally of a distal end of the flexible hypotube 114 may be about 3.0 centimeters.

Upon extending the steerable catheter 116 distally of the flexible hypotube 114, the steerable catheter 116 may be steered about the second bend 128, as described in relation to FIG. 3, and an intravascular device 110 may be deployed distally from the steerable catheter 116. In some embodiments, the intravascular device 110 may be deployed by activating one or more portions of the intravascular device 110 (such as wings, clips, extensions, needles, etc.). In other embodiments, the intravascular device 110 may be deployed by moving the intravascular device 110 longitudinally relative to a sleeve or sheath constraining a radial expansion of the intravascular device 110 (such as with a self-expanding stent or other self-expanding intravascular device 110).

Figure 6:
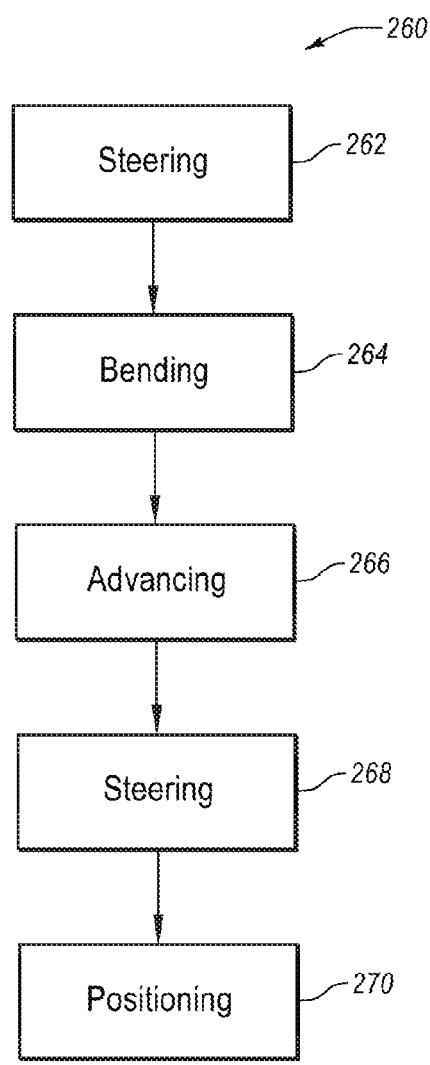
FIG. 6 is a flowchart illustrating a method of delivering an intravascular device, according to the present disclosure.

FIG. 6 illustrates a method 260 for delivering an intravascular device. The method 260 includes steering 262 a portion of an elongated member. For example, steering 262 the portion of the elongated member may include using a steerable catheter to steer a distal end of the elongated member. In other examples, steering 262 the portion of the elongated member may include steering the portion of the elongated member in a bodily cavity. The steering 262 may be performed using one or more cables, wires, sutures, or other force transmission mechanisms to transmit force from a handle to the portion of the elongated member to be deflected. In some embodiments, the elongated member may have one steerable catheter. In other embodiments, the elongated member may have a plurality of steerable catheters. For example, the elongated member may have a steerable catheter that is steerable in at least two planes. In other examples, the elongated member may have a first steerable catheter that is steerable in a first plane and a second steerable catheter that is steerable in a second plane.

The method 260 includes bending 264 a bend region of a flexible hypotube. In some embodiments, the flexible hypotube may preferentially bend in plane. In other embodiments, the flexible hypotube may preferentially bend in a particular direction within a plane, relative to a longitudinal axis of the elongated member. The flexible hypotube may have a plurality of cuts, such as island cuts and/or slits, in the body of the flexible hypotube to direct bending of the flexible hypotube. After bending 264 the flexible hypotube, the method 260 includes advancing 266 at least a portion of the steerable catheter (or catheters) in a distal direction. In some embodiments, the steerable catheter may follow the bend of the flexible hypotube, and a steerable portion of the steerable catheter may be positioned distally beyond a distal end of the flexible hypotube.

The method 260 includes steering 268 a portion of the steerable catheter advanced distally beyond the flexible hypotube. In some embodiments, steering the portion of the steerable catheter that is advanced distally beyond the flexible hypotube includes steering the steerable catheter in a second plane that is non-coplanar from the first plane in which the flexible hypotube bends. For example, steering 268 the steerable catheter after advancing 266 the steerable catheter allows for the compound bend shown in FIG. 3.

Referring again to FIG. 6, the method 260 further includes positioning the distal end of the steerable catheter at or adjacent to a target location. In some embodiments, the target location may be a delivery location for an intravascular device. In other embodiments, the target location may be a repositioning location for a partially deployed intravascular device. In other embodiments, the target location may be an opening to be close by an intravascular device.

Figure 7:
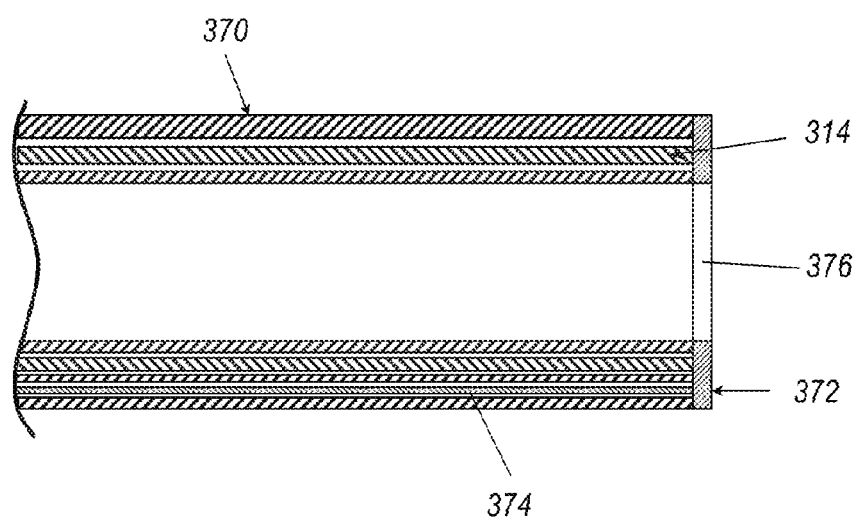
FIG. 7 is a side cross-sectional view of an embodiment of an actively deflectable flexible hypotube, according to the present disclosure.

In at least one embodiment, a flexible hypotube can be actively deflected. As shown in FIG. 7, an intravascular device delivery system according to the present disclosure may include a flexible hypotube 314 that is embedded in a catheter body 370. The catheter body 370 includes at least one lumen 372 through which a tension or steering cable 374 is connected to an end ring 376 welded to the flexible hypotube 314. The proximal ends of the tension cable 374 are attached to a handle to allow the flexible hypotube 314 to deflect when tension force is applied to the tension cable 374.

In some embodiments, an intravascular device delivery system according to the present disclosure may allow delivery of larger intravascular devices and/or through smaller bodily conduits. The intravascular device delivery system may allow for new and/or improved procedures with less risk to the patient and greater ease of operation to the medical professional.

Figure 8:
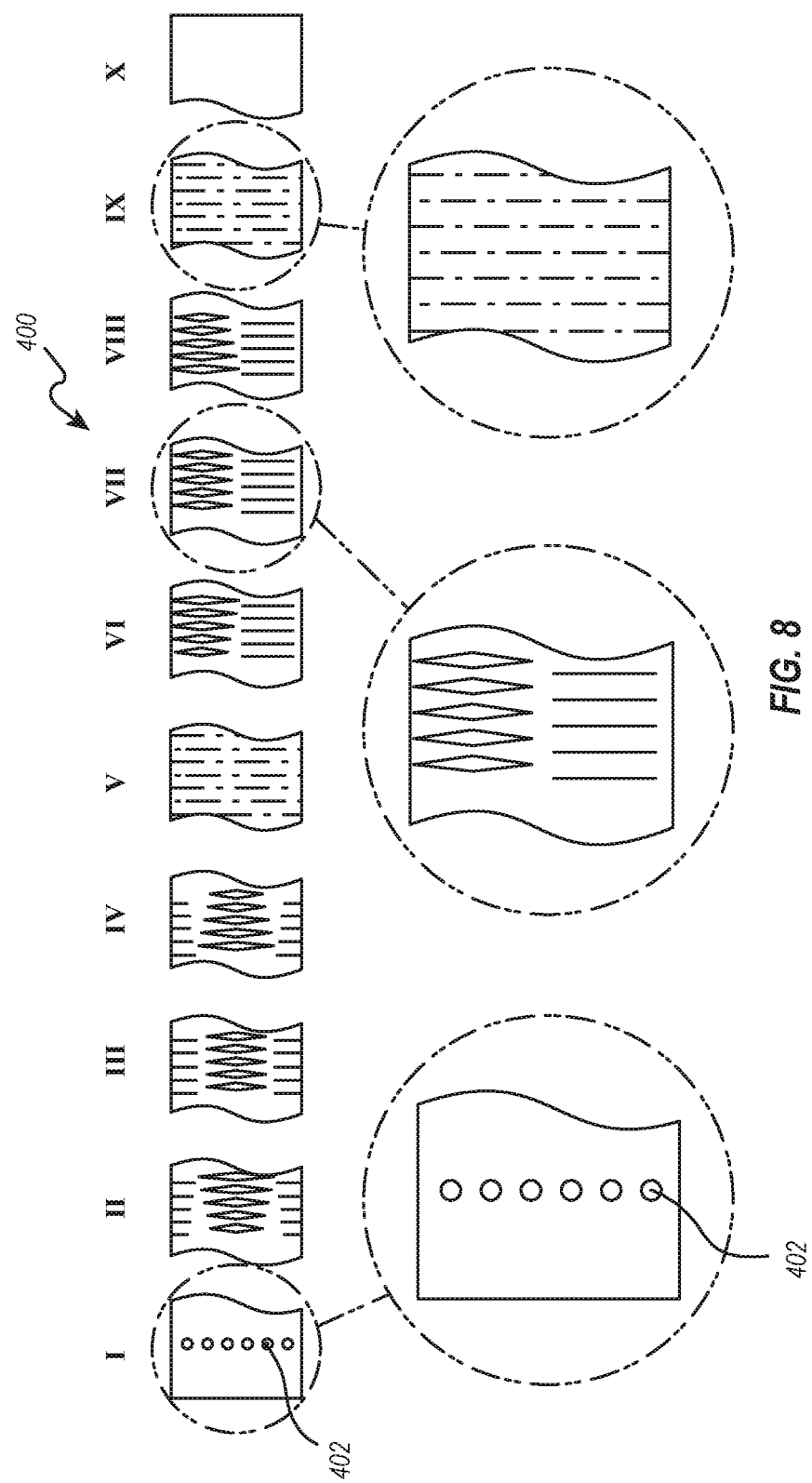
FIG. 8 is a plan view of an embodiment of a cut pattern in a flexible hypotube, according to the present disclosure.

Referring now to FIG. 8 illustrated is a flat view of another cut pattern for a flexible hypotube or catheter according to the present disclosure. The flat view illustrates the pattern of the cuts as though a cylindrical hypotube, for example, were laid flat. In other words, the top edge of the cut pattern and the bottom edge of the cut pattern are connected and continuous in the flexible hypotube, such that the slits and island cuts are oriented circumferential and spaced apart by the spines therebetween. This particular cut pattern allows the flexible hypotube to bend in 2 different planes, while providing desired 1:1 torque control and flexibility. Those planes can be at various angular orientations relative to each other, such as perpendicular or non-perpendicular planes.

As mentioned before, a location of the spine and the design of the slits and cuts define how the hypotube deflects during steering of the intravascular device delivery system. The flexible area of the flexible hypotube, i.e., those areas with the slits and/or cuts, can have various lengths and the slits and cuts of FIGS. 8 and 9 can be the same as other slits and cuts described herein.

As illustrated in FIG. 8, one hypotube 400 can include various sections with and without flexibility patterns or cut patterns based upon the particular movement from the hypotube 400. For instance, some of sections I-X are stiffer than other sections to aid with steering the intravascular device delivery system. As shown, section I includes a number of holes 402, however, a remainder of that section has no cuts or slits. The holes 402 can have a diameter of about 0.5 mm and there can be about 9 holes disposed about the circumference of Section I. Other diameters and number of holes are also possible. For instance, the diameter of the holes 402 can be from about 0.3 mm to about 1 mm. In addition, the number of holes can be greater than or less than 9. For instance, the number of holes can be about 3 to about 12.

Sections II-IX have differing number of slits and/or cuts, while section X has no cuts or slits. The cuts and islands can vary based upon the selected flexibility and torque of the hypotube 400. For instance, as illustrated in FIG. 8, Section II has 12 cut rings, each ring having a width of about 5.5 mm, Section III has similar to section II, but rotated 90 degrees, and with 6 ring, each having a width of about 2.5 mm, Section IV has 12 rings, each having a width of about 5.5 mm, Section V has 14 rings, each having a width of about 13 mm, Section VI has similar to section II, but rotated 90 degrees, and with 12 ring, each having a width of about 5.5 mm, Section VII has 30 cut rings, each ring having a width of about 14.5 mm, Section VIII has a similar to Section IV, but rotated 90 degrees, with 12 cut rings, each ring having a width of about 5.5 mm, Section IX has a similar to Section V with 11 cut rings, each ring having a width of about 10 mm While specific dimension and ring number are provided for hypotube 400, other widths and number of rings are also possible to achieve flexibility and torque transmission for steering through the tortuous anatomy. For instance, in other configurations the number rings can be from about 1 to about 40, with a width of the rings ranging from about 0.5 mm to about 7 mm.

While in many situations the hypotube 400 can be fabricated from a single material, such as stainless steel or shape memory material, such as Nitinol, in some circumstances the hypotube 400 can include a combination of materials. For instance, the deformation in Section II-X may exceed the plastic deformation ability of a stainless steel. A material much better suited for these Sections II-X could be a shape memory material, such as Nitinol with a plastic deformation limit of about 8% compared to stainless steel of <1%. Therefore, in one configuration, different areas or regions of the hypotube 400 can be formed from a material with high deformation limits, such as but not limited to, Nitinol or some other superelastic, pseudoelastic, or shape member material.

Because of the high cost of certain superelastic, pseudoelastic, or shape memory material, those sections where high deformation occurs could be formed from Nitinol, while a remainder of the hypotube can be formed from a less expensive material. For instance, the less expensive material could be stainless steel 304 or 316. Since these materials are dissimilar, a mechanical interlock in a low stress area can be used to join the two different stiffness sections or portions.

Figures 9, 10:
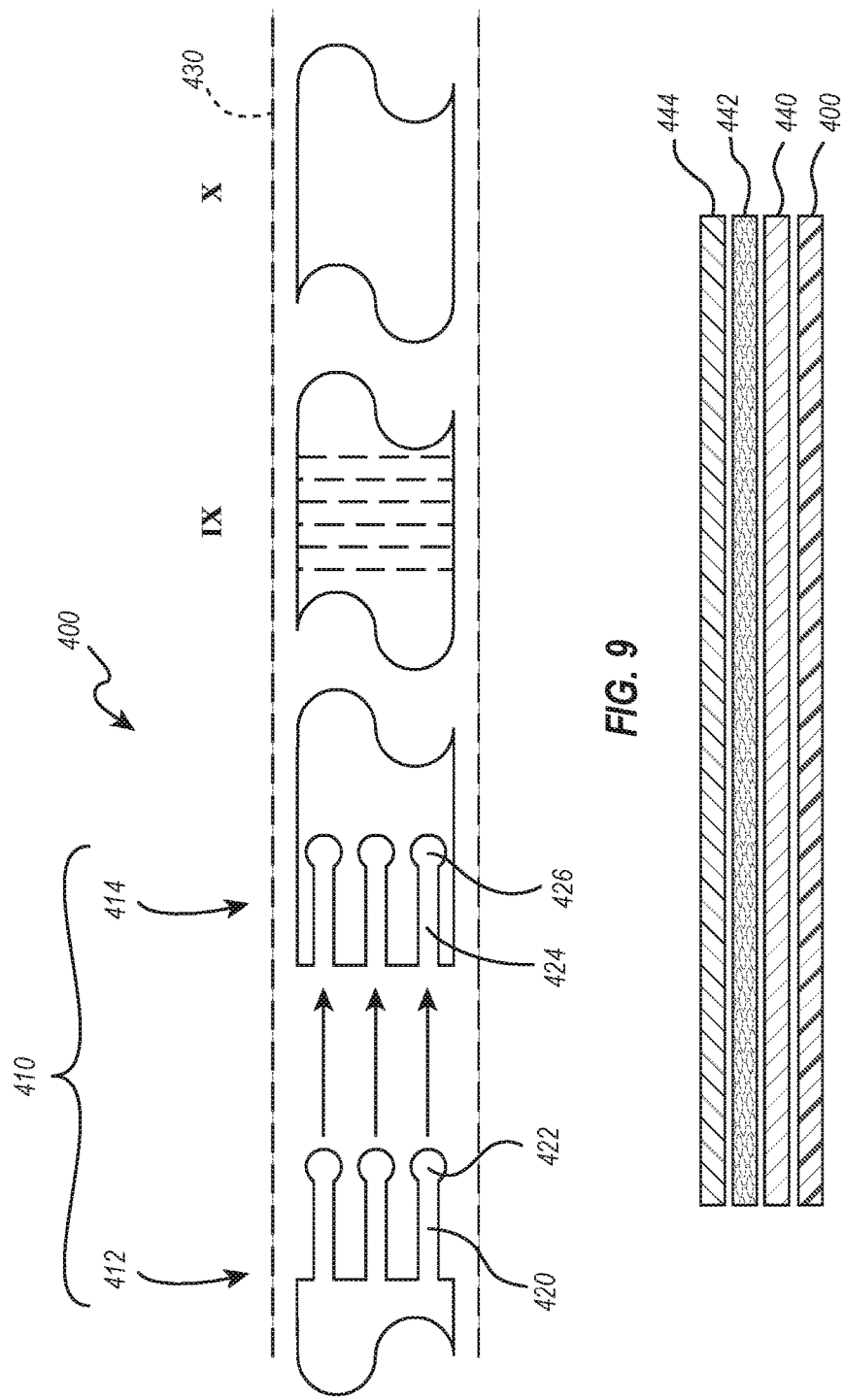
FIG. 9 is a plan view of an embodiment of a mechanical interlock formed in the flexible hypotube, according to the present disclosure.
FIG. 10 is a cross-sectional view of another embodiment of intravascular device delivery system, according to the present disclosure.

To connect the two different sections of the hypotube 400, i.e., a hypotube of a stiffer material and a hypotube of a less stiff material, a mechanical interlock 410 can be used, one example of a mechanical interlock 410 being illustrated in FIG. 9. As with FIG. 8, the mechanical interlock 410 and associated portions of the hypotube are illustrated in a flat view. The flat view illustrates the pattern of the mechanical interlock 410 as though a cylindrical hypotube were laid flat. In other words, the top edge of the mechanical interlock 410 and the bottom edge of the mechanical interlock 410 are connected and continuous in the flexible hypotube. In addition, Section IX and X from FIG. 8 are illustrated in FIG. 9, with Section IX having a different configuration of 171 rings, and an overall length of that section being about 340 mm.

As shown, the mechanical interlock 410 includes a male portion 412 and a female portion 414. The male portion 412 has at least one finger 420, with an enlarged member 422 disposed at an end thereof. The female portion 414 is complementary to the male portion 412 and includes at least one channel 424 with a receiving space 426 at its end to accommodate the enlarged member 422. The two portions of the hypotube 400 connect together when the finger 420 and enlarged member 422 are received in the channel 424 and receiving space 426. For instance, the finger 420 and the enlarged member 422 can be flexible enough to snap into the channel 424 and receiving space 426 having a matching shape.

It is understood that the above-described mechanical interlock 400 is not limited to this specific mechanical interlock described and other mechanical locks can be used as well. For instance, the enlarged member 422 can be a ball or have an elongate form, whether or not curved, square, rhombohedral, triangular, rectangular, circular, oblong, other elliptical, other polygonal, irregular, or combinations thereof. Similarly, the receiving space 426 can accommodate the ball or other elongate form while being complementary to the enlarged member 422. The finger 420 and channel 424 can also have various configurations and orientations.

To aid with securing the two stiffer and less stiff hypotube portions of the hypotube 400 together, the hypotube 400 can be covered with an outer member 430, such one or more braids, outer sheaths or other structures to aid in retaining the finger 420 and the enlarged member 422 in the channel 424 and the receiving space 426, respectively.

In still another configuration, similar to the embodiment of FIG. 7 where the flexible hypotube 314 is embedded in a catheter body 370, instead of incorporating the mechanical interlock into a hypotube that is disposed over a steerable catheter, the function of the flexible hypotube and the steerable catheter can be combined into a catheter having a single hypotube with channels for tension cables used to deflect the catheter. For instance, and as illustrated in FIG. 10, the hypotube 400, such as a combined Nitinol/Stainless steel laser cut hypotube described in FIGS. 8-9 (or another hypotube fabricated from another metal, alloy, or other material), can be covered with tubes 440 to create a space for the tension cable (not shown) responsible for the deflection of the catheter. Those tubes 440 could be polyamide or some other polymer, and could optionally include a polytetrafluoroethylene (PTFE) liner. Alternatively, sacrificial mandrels, which can be removed after forming the catheter, can be placed on an exterior surface of the hypotube 400, with the tubes 440 or mandrels being placed along the axis of the connected hypotubes 400, i.e., a hypotube of a stiffer material and a hypotube of a less stiff material.

Covering the tubes 440 or mandrels can be a braid or coil 442, which helps position the tubes 440 or mandrels and keep them in place when an outer sheath 444, such as a polymeric jacket, is applied to the braid 442 and the tubes 442. The braid or coil 442 limits movement of the tension cable (not shown), i.e., bowing of the tension cable, when high-tension forces are applied during bending and movement of the catheter.

The outer sheath 444 can be an extrusion that is placed over the hypotube 400, the tubes 440, and the braid or coil 442. This extrusion is subsequently covered by a heat shrink tubing, with the extrusion reflowing and connected to the hypotube 400, the tubes 440, and the braid or coil 442. In areas of deflection, a softer outer sheath 444 is provided. The lower durometer of the polymer formed at the deflection areas allows for easier deflection when a pulling force is applied to the tension cable (not shown). Optionally, a hydrophilic coating can be applied to the outer sheath 444. The outer sheath 444 can be a Polyether block amide (PEBAX) or other polymer, with a distal flexible portion of the outer sheath 444, and so the the intravascular device delivery system. The braid 442 and/or outer sheath 444, whether individually or collectively, aid with keeping the mechanical interlock 410 aligned for desired torque transmission, as well as a certain amount of pull or push force. In other configurations, only one of the braid 442 and outer sheath 444 can be included in the hypotube 400.

Turning to another embodiment of the presently described invention, in some circumstances the intravascular device delivery system includes a distal portion with selectable stiffness to aid with steering and positioning the flexible elongated member, such as an elongated member similar to the elongated member 102 in FIG. 1. Selectable stiffness aids, for instance, in positioning an intravascular device within a particular anatomical structure or traversing the tortuous anatomy. By adjusting or varying a distance between two different curves formed by the intravascular device delivery system, enhanced steerability is provided. For instance, the selectably stiffened catheter can have a variable stiffness length between a first curve adjacent the septum, for instance, and a second curve the catheter makes to turn towards another anatomical structure within the heart, such as the Mitral annulus.

Figure 11:
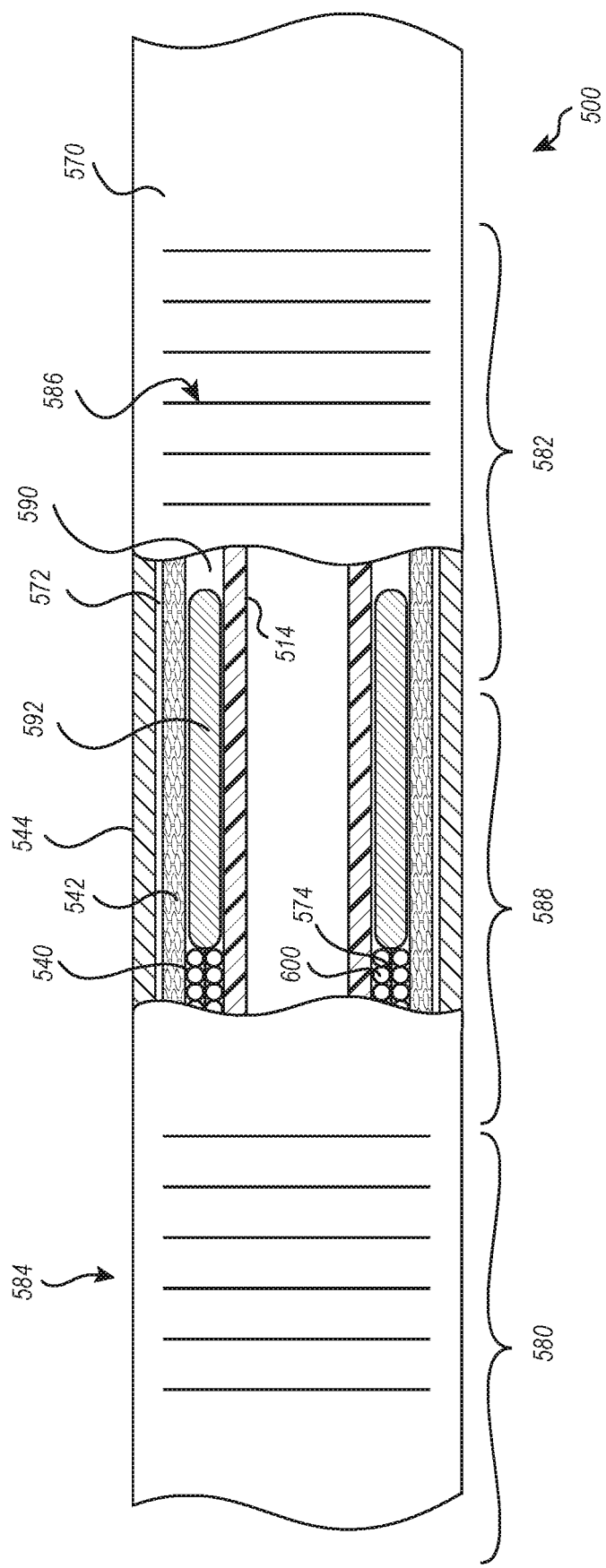
FIG. 11 is a partial cross-sectional view of another embodiment of an intravascular device delivery system, according to the present disclosure.
Figure 12:
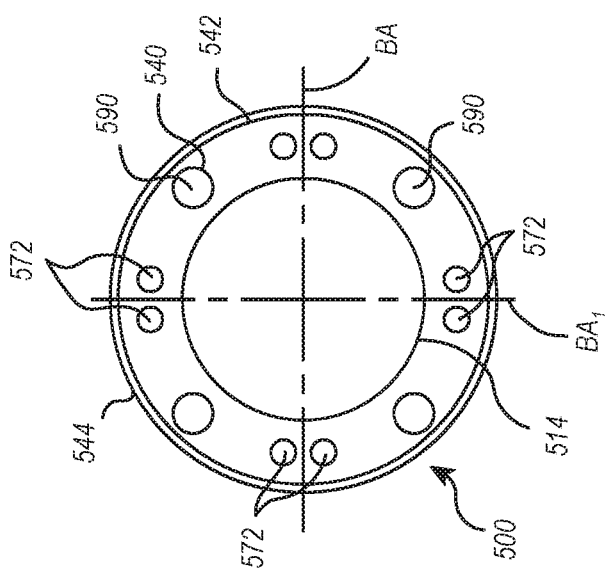
FIG. 12 is a cross-sectional view of the intravascular device delivery system of FIG. 11, according to the present disclosure.
Figure 14:
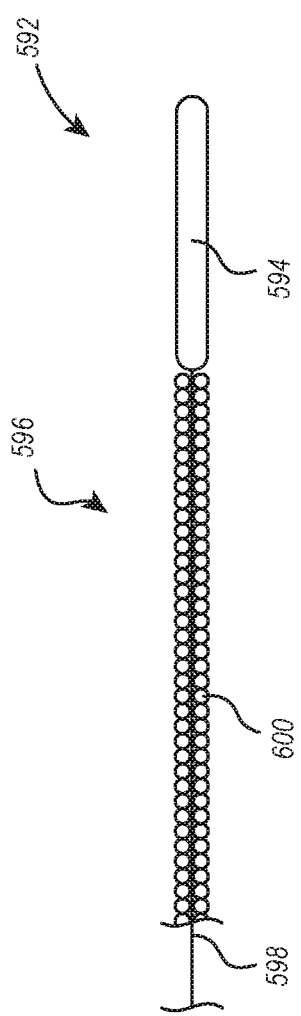
FIG. 14 is a cross-sectional view of a stiffening member, according to the present disclosure.

FIGS. 11 and 12 illustrate a portion of an intravascular device delivery system 500 having a catheter body 570 with at least one lumen 572 through which a tension or steering cable (not shown) is connected or loops around a portion of an end ring (not shown) attached to a flexible hypotube 514, similar to that illustrated in FIG. 7. The structure of the catheter body 570 is similar to the structure of catheter body 370 described herein and so the description of catheter body 370 is applicable to the catheter body 570.

The proximal ends of the tension cable are attached to a handle, such as handle 108 (FIG. 1), to allow the flexible hypotube 514 to deflect when tension force is applied to the tension cable extending through the at least one lumen 572 formed from tubes supported by the hypotube 514, similar to tubes 440, or from sacrificial mandrels that have been removed from the catheter during manufacture. The at least one lumen 572 is illustrated as being positioned at each bending axis $BA_1$ and $BA_2$ of the catheter body 570, with a lumen on opposite sides of the bending axis $BA_1$ and $BA_2$. While two bending axes $BA_1$ and $BA_2$ are illustrated, it would be understood that a greater or lesser number of bending axes could be provided.

The catheter body 570 includes a first region 580 and a second region 582, each with enhanced flexibility because of, respectively, a flexibility pattern 584 and 586. Inclusion of the flexibility patterns 584 and 586 provides different degrees of stiffness to those particular regions 580 and 582 compared with a third region 588 that is formed either without any cut pattern, as illustrated in FIG. 11, or with a flexibility pattern that results in a stiffer area than the first region 580 or the second region 582. The flexibility pattern 584 and 586 can be those illustrated and described in FIGS. 4A, 4B, 8, and 9, or other patterns of cuts, islands, and other structures that provide different stiffness to the catheter body 570. The flexibility pattern 584 and 586 precisely define bending locations and directions, such as allowing the catheter body 570 to bend in two different planes that are perpendicular or transverse to each other, while also defining a distance between the first region 580 and the second region 582, i.e., a length of the third region 588 that can range from about 0 cm to about 5 cm.

Disposed within the catheter body 570 are lumens or channels 590 that receive stiffening members 592. The lumens or channels 590 can be formed from tubes 540 disposed on an exterior of the hypotube 514 or by sacrificial mandrels, which can be removed after forming the catheter body 570. Those tubes 540, like the tubes 440 in FIG. 10, are covered with a braid or coil 542 and optional an outer sheath 544 in a similar manner to the catheter body 370. FIG. 12 illustrates the outer sheath 544 reflown and connected to the hypotube 514, the tubes 540, and the braid or coil 542.

Figure 13A:
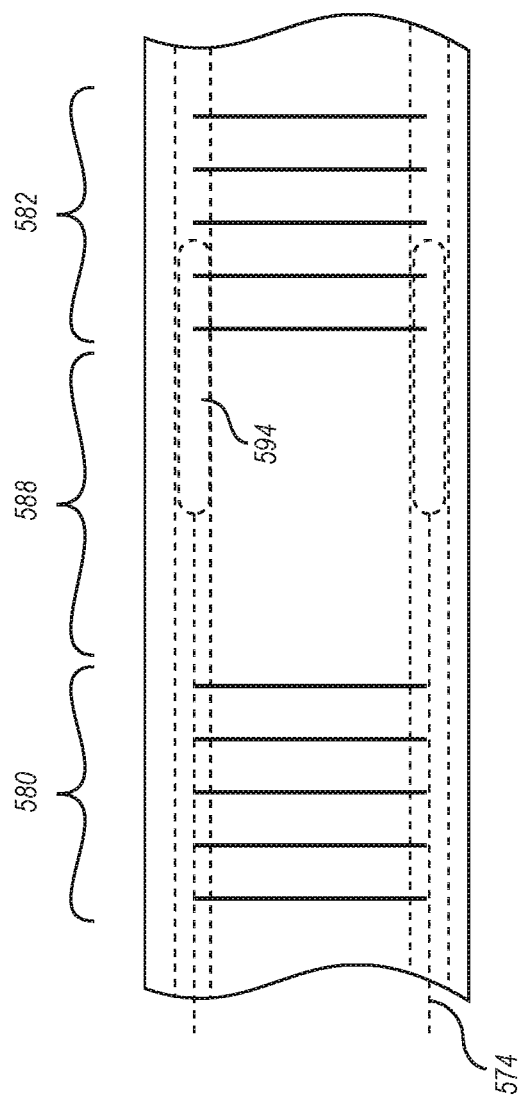
FIGS. 13A and 13B are side views of the intravascular device delivery system of FIG. 11, according to the present disclosure
Figure 13B:
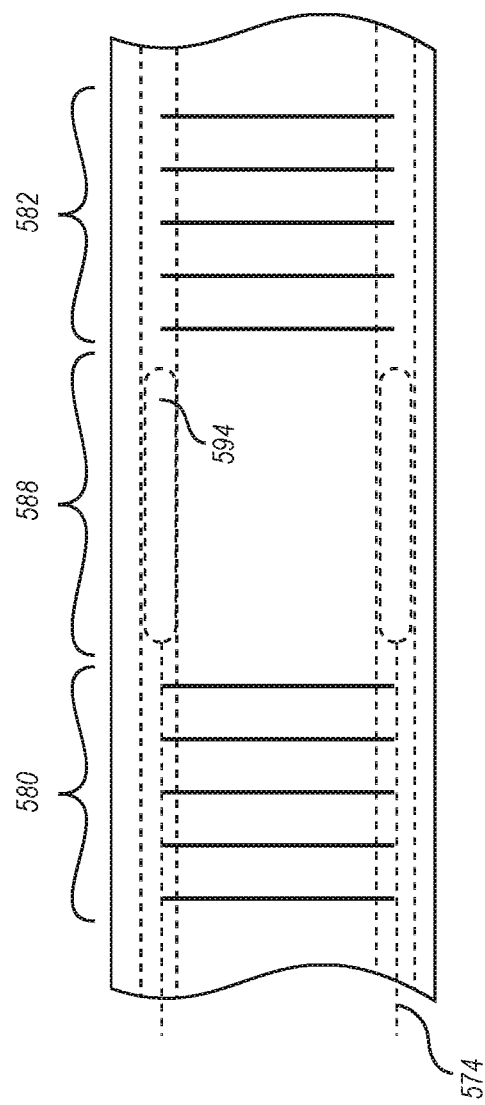

The stiffening members 592 are elongated and movable within the lumens 590. In one position, illustrated in FIG. 13A, the stiffening members 592 at least partly overlap with the flexibility pattern 586, while in another position the stiffening members 592 are retracted from and separated from the flexibility pattern 586, as illustrated in FIG. 13B. When overlapping the flexibility pattern 586, the stiffness of stiffening member 592 limits bending at the second region 582. To limit bending, an elongate shaft member 594 of the stiffening member 592 has a stiffness greater than the stiffness of the second region 582. For instance, the elongate shaft member 594 can be fabricated from a hardened metal or alloy, such as steel, or any other stiff material, such as fiber reinforced polymers, ceramics, glass organic or inorganic materials, or composites.

By pulling an actuating member 596 proximally, such as with the handle 108 (FIG. 1), the stiffening members 592 is withdrawn from alignment with the flexibility pattern 586 and they will be uncovered. The second region 584 can then bend or deflect when force is applied to the tension or steering cables 574. In contrast, when the actuating member 596 is advanced distally within the lumen 590, the elongate shaft member 594 again overlaps with the flexibility pattern 586 and the stiffness of the second region 582 is increased.

The actuating member 596 can include a flexible pull member 598, such as a pull cable, flexible rod, etc., and a compression member 600 disposed around the flexible pull member 598. The flexible pull member 598 has sufficient strength in tension to move the elongate shaft member 594 proximally, while the compression member 600, such as a compression coil, flexible metallic or polymeric tube, or other structure, which provides sufficient rigidity or column strength to transfer a force applied to the elongate shaft member 594 in a distal direction to advance the elongate shaft member 594 within the lumen 590.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A method for positioning an end of an intravascular device delivery system, the method comprising:
    steering a steerable catheter in a first plane, the steerable catheter being positioned radially inside a flexible hypotube;
    bending the flexible hypotube in a direction within the first plane to create a first bend in the flexible hypotube, wherein bending the flexible hypotube in the direction includes expanding one or more slit cuts in a bend region of the flexible hypotube;
    advancing the steerable catheter distally relative to the flexible hypotube and distal of a distal end of the flexible hypotube;
    steering the steerable catheter in a second plane; and
    positioning a distal end of the steerable catheter at a target location.

2. The method of claim 1, wherein the first plane and second plane are non-coplanar.

3. The method of claim 1, wherein advancing the steerable catheter further comprises moving a first tab of the steerable catheter within a first slot of the flexible hypotube.

4. The method of claim 1, further comprising varying a position of a stiffening member disposed within a lumen associated with the steering catheter to adjust a stiffness of the steering catheter.

5. The method of claim 1, wherein the steering catheter comprises at least one island cut and at least one slit cut for a flexibility pattern, wherein varying the position of a stiffening member comprises slidably disposing the stiffening member within a lumen between a first position at least partially overlapping the flexibility pattern and a second position spaced from the flexibility pattern.

6. A method for positioning an end of an intravascular device delivery system, the method comprising:
    steering a steerable catheter in a first plane, the steerable catheter being positioned radially inside a flexible hypotube;
    bending the flexible hypotube in the first plane to create a first bend in the flexible hypotube;
    advancing the steerable catheter distally relative to the flexible hypotube and distal of a distal end of the flexible hypotube, wherein advancing the steerable catheter further comprises moving a first tab of the steerable catheter within a first slot of the flexible hypotube;
    steering the steerable catheter in a second plane; and
    positioning a distal end of the steerable catheter at a target location.

7. The method of claim 6, wherein the first plane and second plane are non-coplanar.

8. The method of claim 6, further comprising varying a position of a stiffening member disposed within a lumen associated with the steering catheter to adjust a stiffness of the steering catheter.

9. The method of claim 6, wherein the steering catheter comprises at least one island cut and at least one slit cut for a flexibility pattern, wherein varying the position of a stiffening member comprises slidably disposing the stiffening member within a lumen between a first position at least partially overlapping the flexibility pattern and a second position spaced from the flexibility pattern.

10. A method for positioning an end of an intravascular device delivery system, the method comprising:
    steering a steerable catheter in a first plane, the steerable catheter being positioned radially inside a flexible hypotube;
    bending the flexible hypotube in the first plane to create a first bend in the flexible hypotube;
    advancing the steerable catheter distally relative to the flexible hypotube and distal of a distal end of the flexible hypotube;
    steering the steerable catheter in a second plane;
    positioning a distal end of the steerable catheter at a target location; and
    varying a position of a stiffening member disposed within a lumen associated with the steering catheter to adjust a stiffness of the steering catheter,
    wherein the steering catheter comprises at least one island cut and at least one slit cut for a flexibility pattern, wherein varying the position of the stiffening member comprises slidably disposing the stiffening member within a lumen between a first position at least partially overlapping the flexibility pattern and a second position spaced from the flexibility pattern.

11. The method of claim 10, wherein the first plane and second plane are non-coplanar.

12. The method of claim 10, wherein advancing the steerable catheter further comprises moving a first tab of the steerable catheter within a first slot of the flexible hypotube.

* * * * *